United States Patent [19]

Meyer

[11] Patent Number: 4,960,414

[45] Date of Patent: Oct. 2, 1990

[54] TRAINING PANTS

[76] Inventor: Sandra L. Meyer, 2227 W. Dayton Ave., Fresno, Calif. 93705

[21] Appl. No.: 408,226

[22] Filed: Sep. 18, 1989

[51] Int. Cl.⁵ ............................................. A61F 13/16
[52] U.S. Cl. .................................. 604/395; 604/394
[58] Field of Search .................. 604/358, 374, 385.1, 604/386, 387, 389, 391, 393–397

[56] References Cited

U.S. PATENT DOCUMENTS

| | | | |
|---|---|---|---|
| 580,406 | 4/1897 | Kleinert | 604/386 |
| 2,144,728 | 1/1939 | Paul et al. | 604/396 |
| 2,290,110 | 7/1942 | McGraw | 604/389 |
| 2,654,367 | 10/1953 | Turnham | 604/394 |
| 2,834,347 | 5/1958 | Connally | 604/385.1 |
| 2,841,147 | 7/1958 | McLaurin | 604/358 |
| 3,029,816 | 4/1962 | Neils | 604/385.1 |
| 3,324,856 | 6/1967 | Young | 604/394 |
| 3,368,562 | 2/1968 | Vogt | 604/385.1 |
| 3,756,878 | 9/1973 | Willot | 604/389 |
| 4,022,212 | 5/1977 | Lovison | 604/391 |
| 4,114,621 | 9/1978 | Mims, Jr. | 604/395 |
| 4,122,552 | 10/1978 | Tedford | 604/389 |
| 4,145,763 | 3/1979 | Abrams et al. | 604/391 |
| 4,576,599 | 3/1986 | Lipner | 604/389 |
| 4,615,695 | 10/1986 | Cooper | 604/385.1 |
| 4,619,649 | 10/1986 | Roberts | 604/396 |
| 4,641,381 | 2/1987 | Heran et al. | 2/400 |
| 4,710,188 | 12/1987 | Runeman | 604/358 |
| 4,743,241 | 5/1988 | Igaue | 604/385.1 |
| 4,828,555 | 5/1989 | Hermansson | 604/385.1 |

FOREIGN PATENT DOCUMENTS

| 0022253 | of 1894 | United Kingdom | 604/385.1 |
|---|---|---|---|
| 0005556 | of 1907 | United Kingdom | 604/385.1 |

Primary Examiner—Stephen C. Pellegrino
Assistant Examiner—Sharon Rose

[57] ABSTRACT

A low cost disposable pair of training pants formed substantially entirely of paper. These pants include an outer paper sheet that defines the waist opening and leg openings, and an inner paper liner secured to inner surfaces of the outer sheet. The liner is selected for its water absorbency characteristics. The outer sheet may be selected primarily for its strength and flexibility.

1 Claim, 1 Drawing Sheet

TRAINING PANTS

BACKGROUND AND SUMMARY OF THE INVENTION

This invention relates to low cost disposable training pants adapted for use by small children during the toilet training period. The training pants are intended to be used once (or only a few times) and then thrown away. They could be made in different colors (e.g. blue or pink) and patterns.

Busy working mothers would find these training pants especially useful because they would avoid the clothes washing problem associated with conventional cloth training pants. The proposed training pants are made substantially entirely out of paper, which is a biodegradable material that can be thrown away without the long term earth contamination problems associated with most plastic materials.

In some respects my proposed training pants are similar to the training pants shown in U.S. Pat. No. 4,615,695 to R. Cooper, and U.S. Pat. No. 4,641,381 to W. Heran, and U.S. Pat. No. 4,743,241 to T. Igaue et al. However, the proposed training pants are believed to be simpler and less costly to manufacture than the pants shown in those patents.

THE DRAWINGS

DESCRIPTION OF A PREFERRED EMBODIMENT OF THE INVENTION

Figure 1:
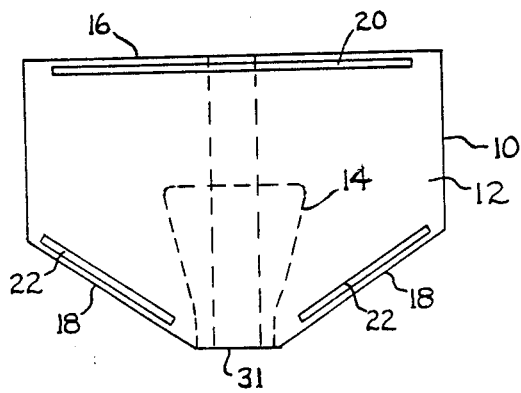
FIG. 1 is a front elevational view of a pair of training pants constructed according to the invention.

FIG. 1 shows a pair of training pants 10 formed of an outer paper sheet 12, and an inner paper liner 14. FIG. 1 shows the pants in a flat folded condition, with liner 14 located within sheet 12 between the front and rear walls of the pants. Numeral 16 designates generally the waist opening of the pants, whereas numerals 18 designate the leg openings for the pants. Elastic strips 20 are stitched to the front and rear walls of the pants outer sheet 12 near the sheet upper edge, i.e. partially encircling the waist opening 16. Elastic strips 22 are stitched to the front and rear walls of the pants outer sheet 12 near the sheet lower edge, i.e. partially encircling leg openings 18.

Figure 2:
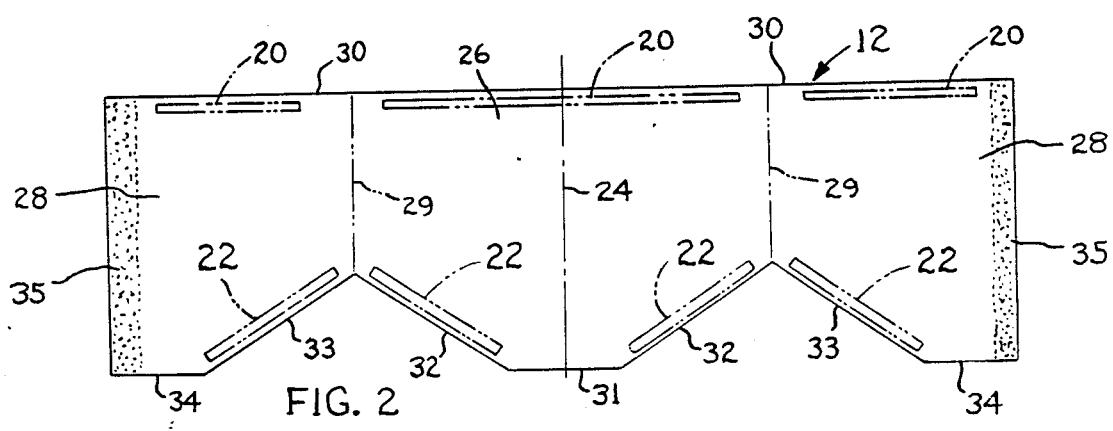
FIG. 2 is a plan view of a paper sheet used in the FIG. 1 pair of pants.

Elastic strips 20 and 22 are preferably in slightly stretched conditions when they are stitched to sheet 12. The elastic strips therefore tend to resiliently contract the sheet 12 material so as to elastically reduce the sizes of the associated openings 16 and 18 for thus fitting the pants to the child's body. The elastic strips are shown in dashed lines in FIG. 2, primarily to indicate the strip locations on the flat sheet. Strips 20 and 22 may be stitched to sheet 12 while the sheet is in the flat state (FIG. 2), or after the sheet has been formed into a three dimensional configuration.

In its flat state, sheet 12 has an imaginary vertical centerline 24 subdividing the sheet into two similar half sections. The sheet includes a central panel 26 centered on centerline 24, and two side panels 28 extending laterally from side edges 29 of the central panel.

The three panels 26, 28, 28 are actually merely sections of a single paper sheet 12 that is homogeneous along its vertical and horizontal dimensions. The three panels have a common upper edge 30 extending normal to imaginary centerline 24. Central panel 26 has a lower central edge 31 and two outboard lower edges 32 angling outwardly and upwardly. Each side panel 28 has a downwardly angled edge 33 and a straight edge 34 extending generally normal to centerline 24.

At least one of the outer edge areas 35 of side panels 28 has an adhesive thereon, such that when the two side panels are folded behind central panel 26 along fold lines 29 the adhesive surface(s) will join the sheet into a three dimensional pants configuration. Edges 32 and 33 will form leg openings, whereas upper edge 30 will form a waist opening.

Figure 3:
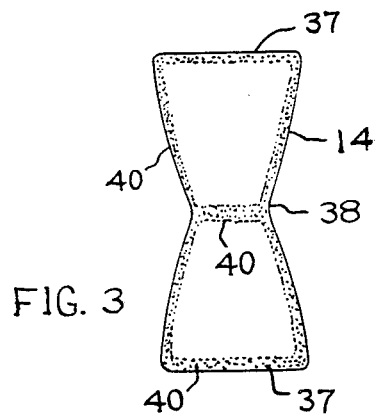
FIG. 3 is a plan view of a paper liner used in the FIG. 1 pair of pants.

Liner 14 (FIG. 3) has an hour glass configuration that forms relatively wide end areas 37 and a relatively narrow central neck area 38. Face areas 40 of the liner have an adhesive thereon for attaching the liner to the inner surfaces of sheet 12. The liner 14 is oriented so that narrow neck area 38 extends along the lower central edge 31 of central panel 26 when the liner is attached to the inner surface of sheet 12. The liner will be positioned on central panel 26 and folded around neck 38 prior to the step of folding side panels 28 around fold lines 29. Liner 14 will be formed of one or more paper sheets selected for water absorbency.

The FIG. 1 training pants are formed primarily of paper (except for elastic strips 20 and 22); therefore they can be disposed of via normal trash collection procedures without worry over possible earth contamination effects.

The manufacturing cost for the illustrated pants should be relatively low, such that they can be discarded after only one or two wearings (when soiled) without great consumer expense.

I claim:

1. A child's disposable biodegradable training pants comprising an outer paper sheet, an inner paper liner, and a plural number of elastic strips attached to upper and lower edge areas of said outer sheet;

said outer sheet having an imaginary vertical centerline (24); said outer sheet including a central panel (26) centered on said vertical centerline, and two side panels (28) extending laterally from said central panel; said central panel and said side panels having a common upper edge (30) extending normal to the vertical center line, said side panels having outer edge areas (35) extending parallel to the vertical centerline;

said central panel having a straight lower central edge (31) extending generally normal to the vertical centerline, and generally straight outboard edges (32) angling outwardly and upwardly from said central edge; each side panel having a generally straight lower inboard edge (33) that angles downwardly and outwardly from the central panel, and an outboard edge that is generally normal to the vertical centerline;

said elastic strips comprising individual elastic strips extending along said outboard edges of the central panel and said inboard edges of the side panels;

said paper liner having an hour glass configuration that forms a relatively narrow central neck area (38) adapted to extend long the lower central edge of the central panel when the liner is attached to the inner surface of the outer sheet;

said outer edge areas (35) of the side panels being adhesively secured together; said paper liner being adhesively secured along its perimeter edge to the central panel and the side panels.

* * * * *